United States Patent [19]

Schaus et al.

[11] Patent Number: 4,753,880
[45] Date of Patent: Jun. 28, 1988

[54] METHOD OF SELECTION FOR SPIRAMYCIN RESISTANCE IN STREPTOMYCES

[75] Inventors: Nancy A. Schaus; Patricia J. Solenberg, both of Indianapolis, Ind.

[73] Assignee: Eli Lilly and Company, Indianapolis, Ind.

[21] Appl. No.: 685,677

[22] Filed: Dec. 24, 1984

[51] Int. Cl.[4] .................. C12N 15/00; C12N 1/20; C07H 15/12
[52] U.S. Cl. .................. 435/172.3; 435/253; 435/320; 435/872; 435/886; 536/27; 935/11; 935/29; 935/75
[58] Field of Search .................. 435/172.3, 317, 886; 536/27; 935/9, 29, 52, 75

[56] References Cited

U.S. PATENT DOCUMENTS 4,513,086  4/1985  Fayerman et al. .................. 435/317

OTHER PUBLICATIONS

Buchanan et al. in *Bergey's Manual of Determinative Bacteriology*, 8th ed. pp. 727 and 747.
Thompson et al., 1980 *Nature 286*; 525–527.
Thompson et al., 1982, *Gene 20*: 51–62.
Thompson et al., 1982, *J. Bacteriol. 15*: 668–677.
Murakami et al., 1983, *J. Antibiotics 36*: 1305–1311.
Fujisawa and Weisblum, 1981. *J. Bacteriol. 146*: 6211.
Weisblum, B. (1983) Inducible Resistance to Macrolides, Lincosamides, and Streptogramin Type-B Antibiotics: The Resistance Phenotype, Its Biological Diversity, and Structural Elements that Regulate Expression, In Beckwith, J., Davies, J., and Gallant, J. (Eds.), Gene Function in Procaryotes, Cold Spring Harbor Laboratory, Cold Spring Harbor, NY pp. 91–121.
Journal of Clinical Microbiology, Jun. 1980, pp. 728–736.

*Primary Examiner*—Thomas G. Wiseman
*Assistant Examiner*—Thomas D. Mays
*Attorney, Agent, or Firm*—Gerald V. Dahling; Leroy Whitaker

[57] ABSTRACT

A novel method of selecting Streptomyces recombinant DNA-containing host cells and vectors useful in the method are described. The vectors confer spiramycin resistance to sensitive Streptomyces host cells and thus provide a convenient method of selecting Streptomyces transformants. The novel spiramycin resistance-conferring gene described can be isolated on an ~3.8 kb BclI restriction fragment from plasmid pNAS105. Plasmid pNAS105 can be isolated from *Streptomyces griseofuscus* C581/pNAS105 (NRRL 15919).

32 Claims, 6 Drawing Sheets

Restriction Site and Function Map of Plasmid pNAS105 (14 kb)

Restriction Site and Function Map of Plasmid pNAS105
(14 kb)

Restriction Site and Function Map of Plasmid pIJ702
(5.65 kb)

Restriction Site and Function Map of Plasmid pNAS108
(9.5 kb)

Restriction Site and Function Map of Plasmid pNAS109
(9.5 kb)

Restriction Site and Function Map of Plasmid pNAS107
(10.35 kb)

Restriction Site and Function Map of Plasmid pNAS106
(12.5 kb)

METHOD OF SELECTION FOR SPIRAMYCIN RESISTANCE IN STREPTOMYCES

SUMMARY OF THE INVENTION

The present invention is a method for selecting a recombinant DNA-containing Streptomyces host cell. The invention further comprises recombinant DNA cloning vectors and transformants useful in executing the method.

The present method provides spiramycin resistance-conferring cloning vectors for use in Streptomyces. The development and exploitation of recombinant DNA technology in Streptomyces is dependent upon the availability of selectable genetic markers on suitable cloning vectors. This development has been somewhat retarded by the low number of selectable markers presently available for use in Streptomyces. The present invention is useful and especially important in that it expands the number of selectable markers suitable for such use.

The vectors of the present method are particularly useful because they are small, versatile and can be transformed and selected in any Streptomyces cell that is sensitive to spiramycin and permissive for the plasmid pIJ702 replicon. Streptomyces provides over half of the clinically important antibiotics and thus is a commercially significant group. The present invention provides new and useful cloning systems and vectors for this industrially important group and allows for the cloning of genes both for increasing the yields of known antibiotics, as well as for the production of new antibiotics and antibiotic derivatives.

The present invention further provides a method of selecting Streptomyces transformants from a background of untransformed cells. The method allows one to add non-selectable DNA to the present vectors, transform Streptomyces with the modified vectors and select spiramycin-resistant transformants containing this otherwise non-selectable DNA. Since transformation is a very low frequency event, such a functional test is a practical necessity for determining which cell(s), of among the millions of cells, has acquired the transforming DNA.

For purposes of the present invention, as disclosed and claimed herein, the following terms are defined below.

Recombinant DNA Cloning Vector—any autonomously replicating or integrating agent, including, but not limited to, plasmids, comprising a DNA molecule to which one or more additional DNA segments can be or have been added.

Transformation—the introduction of DNA into a recipient host cell that changes the genotype and results in a change in the recipient cell.

Transformant—a recipient host cell that has undergone transformation.

Sensitive Host Cell—a host cell that cannot grow in the presence of a given antibiotic without a DNA segment that provides resistance thereto.

Restriction Fragment—any linear DNA molecule generated by the action of one or more restriction enzymes.

Phasmid—a recombinant DNA vector that may act as a phage or as a plasmid.

$Tsr^R$—the thiostrepton-resistant phenotype tsr—the thiostrepton resistance gene mel—the tyrosinase gene $Spi^R$—the spiramycin-resistant phenotype

DETAILED DESCRIPTION OF THE INVENTION

The present invention is a method for selecting a recombinant DNA-containing Streptomyces host cell, said method comprising:

(1) transforming a spiramycin-sensitive, restrictionless Streptomyces host cell with a recombinant DNA cloning vector capable of autonomous replication in said Streptomyces host cell, said vector comprising a constructed DNA sequence that confers resistance to spiramycin, and (2) culturing said transformed cell under conditions suitable for selection for spiramycin resistance, subject to the limitation that said host cell is susceptible to transformation, cell division and culture. The present invention further comprises the vectors and transformants used to practice the aforementioned method.

The present method for selecting Streptomyces transformants by the spiramycin-resistant phenotype is best exemplified by transforming *Streptomyces griseofuscus* with plasmid pNAS105 and selecting the resulting transformants on spiramycin-containing media. Plasmid pNAS105 comprises a novel spiramycin resistance-conferring gene that was isolated from *Streptomyces ambofaciens*. and cloned into plasmid pIJ702. Plasmid pNAS105 has been demonstrated to confer resistance to the macrolide antibiotic spiramycin. It may also confer resistance to other macrolide antibiotics. Such cross-resistance has been demonstrated by Fujisawa and Weisblum, 1981, *J. Bacteriol.* 146: 621-631. Plasmid pNAS105 can be obtained from *Streptomyces griseofuscus*/pNAS105, a strain deposited and made part of the permanent stock culture collection of the Northern Regional Research Laboratory, Agricultural Research Serivce, 1815 North University St., U.S. Department of Agriculture, Peoria, Ill. 61604, under the accession number NRRL 15919. A restriction site and function map of plasmid pNAS105 is presented in FIG. 1 of the accompanying drawings.

Figure 1:
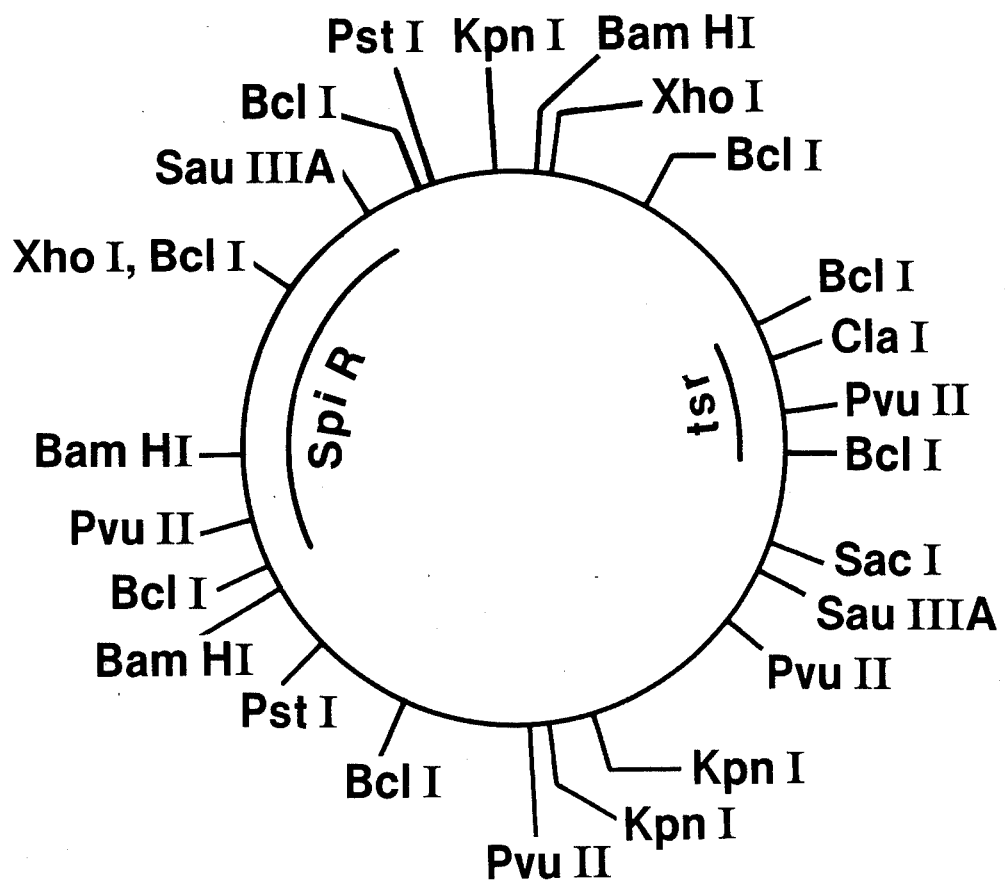
FIG. 1 shows the restriction site and function map of plasmid pNAS105.
Figure 2:
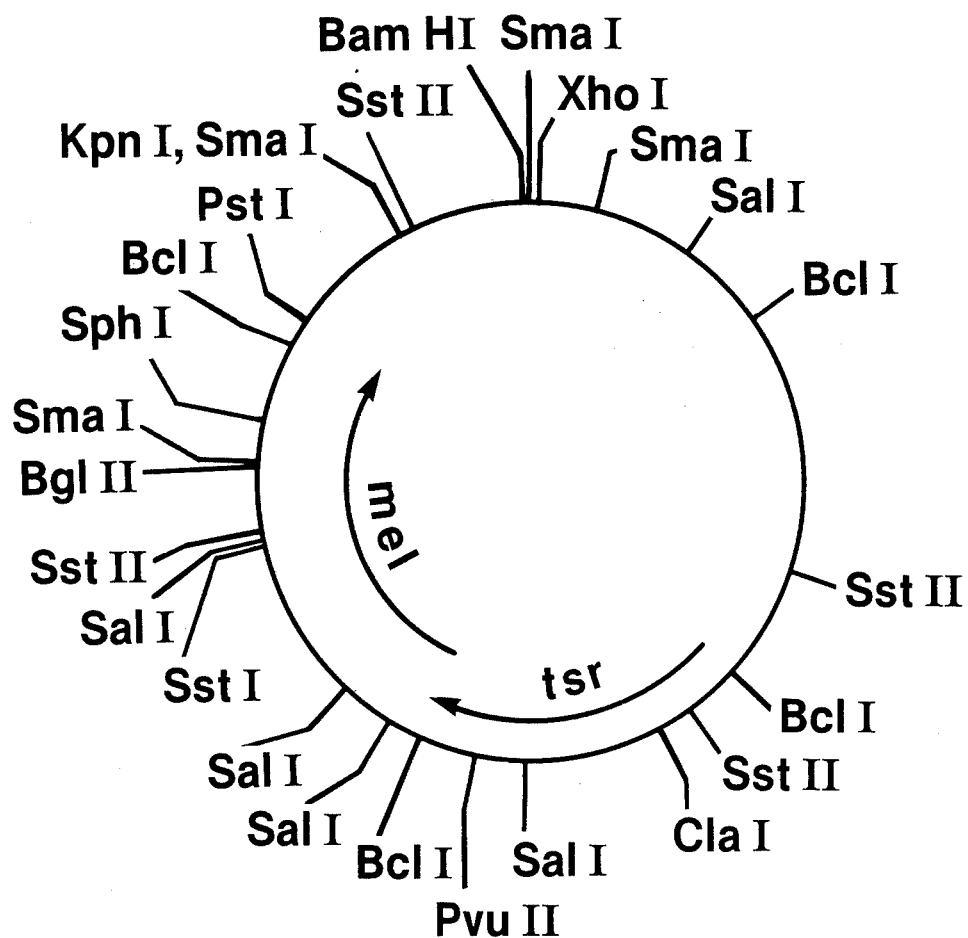
FIG. 2 shows the restriction site and function map of plasmid pIJ702.
Figure 3:
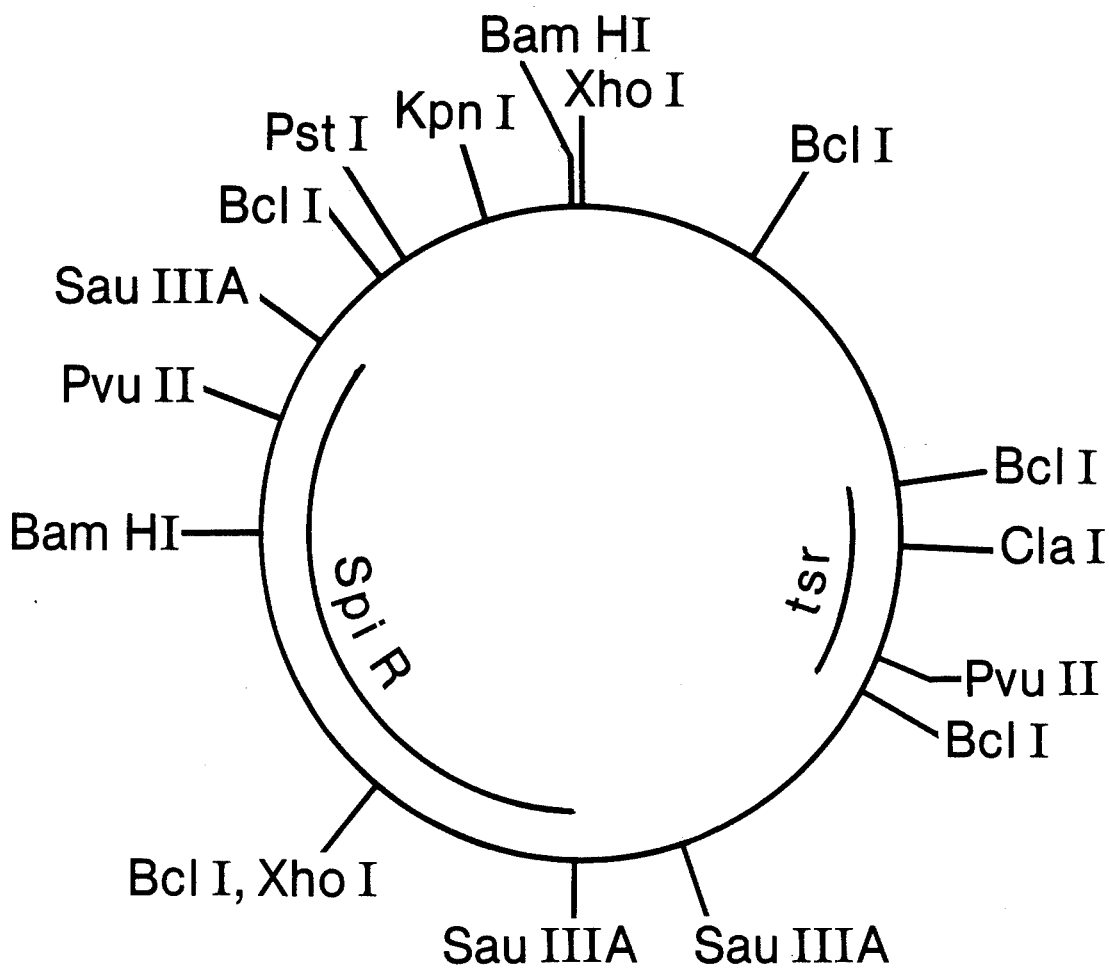
FIG. 3 shows the restriction site and function map of plasmid pNAS108.
Figure 4:
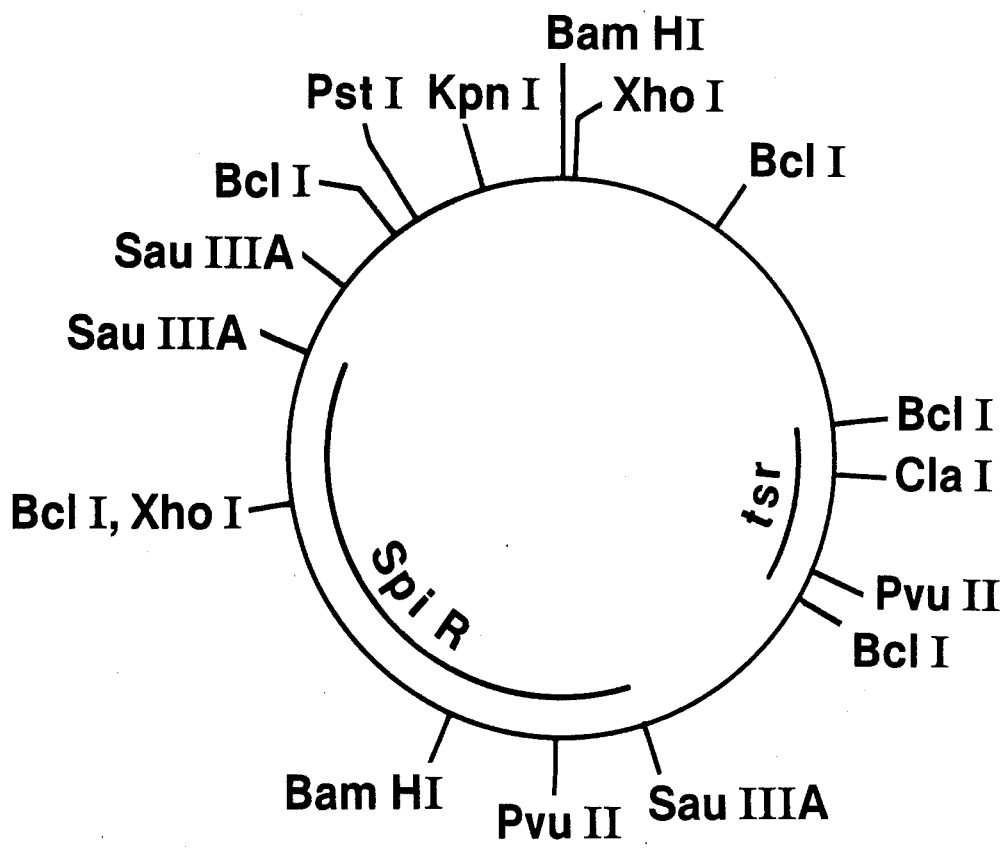
FIG. 4 shows the restriction site and function map of plasmid pNAS109.

As shown in FIG. 1, the ~3.8 kb BclI restriction fragment of plasmid pNAS105 contains the entire spiramycin resistance-conferring gene of the present invention. Knowing the location of the spiramycin resistance-conferring gene allows for construction of other cloning vectors also useful in the present method. Thus, plasmids pNAS108 and pNAS109 were constructed by inserting the ~3.8 kb spiramycin resistance-conferring BclI restriction fragment into the BglII site of plasmid pIJ702, thus inactivating the tyrosinase gene present in plasmid pIJ702. The two resultant plasmids, pNAS108 and pNAS109, differ only with respect to the orientation of the inserted fragment. The plasmid pIJ702 starting material can be obtained from *Streptomyces lividans*/pIJ702, a strain deposited and made part of the permanent stock culture collection of the American Type Culture Collection, 12301 Parklawn Dr., Rockville, Md. 20852, under the accession number ATCC 39155. Restriction site and function maps of plasmids pIJ702, pNAS108 and pNAS109 are respectively presented in FIGS. 2, 3 and 4 of the accompanying drawings.

Figure 5:
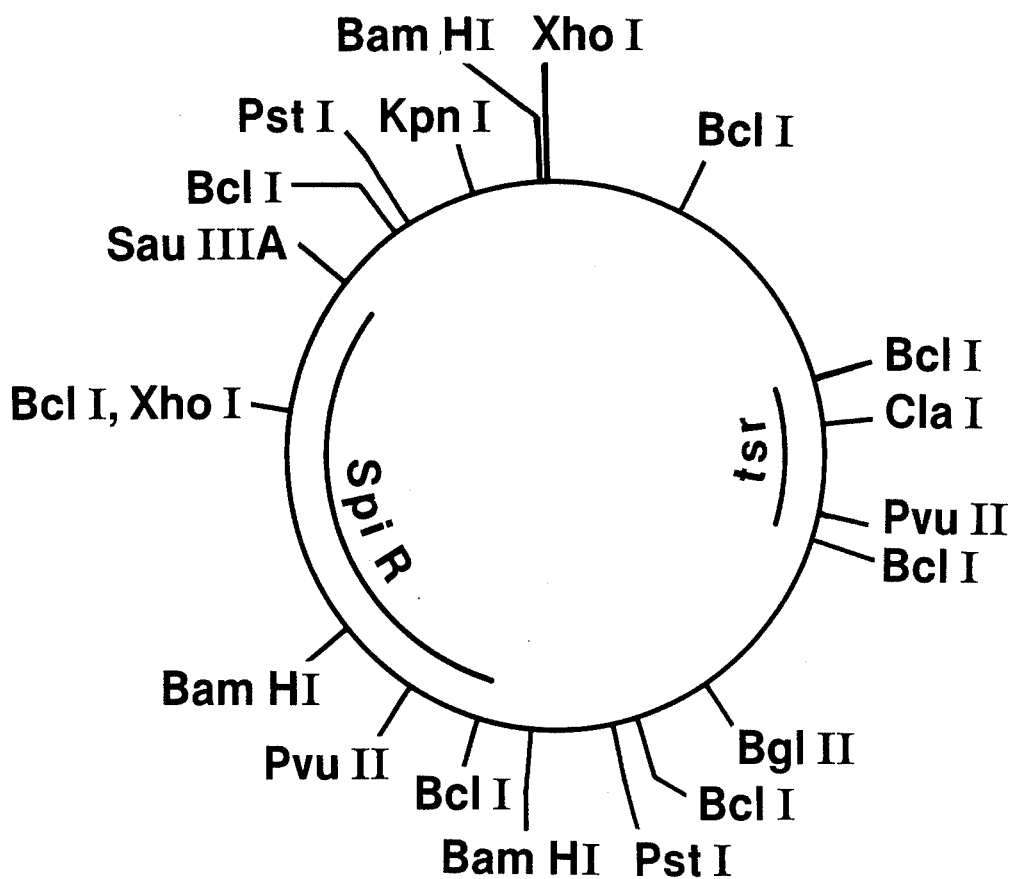
FIG. 5 shows the restriction site and function map of plasmid pNAS107.

Plasmids pNAS107 and pNAS107A were constructed by inserting the ~4.7 kb PstI restriction fragment of plasmid pNAS105 into the PstI site of plasmid pIJ702. Again, two plasmids resulted because of the two possible orientations of the inserted fragment. These plasmids are useful in the present method because the inserted fragment contains the ~3.8 kb BclI spiramycin resistance-conferring restriction fragment of plasmid pNAS105. A restriction site and function map of plasmid pNAS107 is presented in FIG. 5 of the accompanying drawings.

Figure 6:
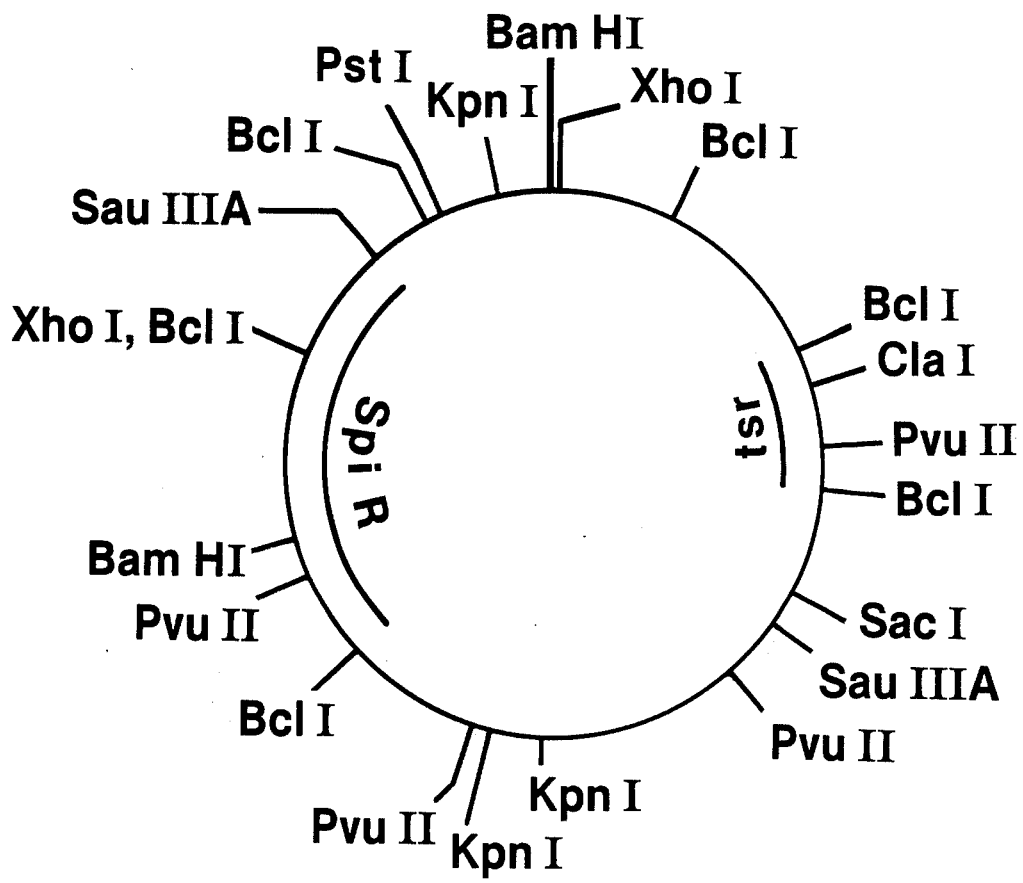
FIG. 6 shows the restriction site and function map of plasmid pNAS106.

Derivative vectors that further exemplify the invention can also be constructed. For example, BclI deletion of plasmid pNAS105 results in illustrative plasmid pNAS106, a plasmid from which additional derivatives can also be made. A restriction site and function map of plasmid pNAS106 is presented in FIG. 6 of the accompanying drawings.

Restriction fragments used to construct vectors illustrative of the present invention can be conventionally modified to facilitate ligation. For example, molecular linkers can be provided to a particular spiramycin resistance gene-containing restriction fragment or to DNA comprising replication functions. Thus, specific sites for subsequent ligation can be constructed conveniently. In addition, the various spiramycin resistance gene-containing restriction fragments and origin of replication sequences can be modified by adding, eliminating or substituting certain nucleotides to alter characteristics and to provide a variety of restriction sites for ligation of DNA. Those skilled in the art understand nucleotide chemistry and the genetic code and thus which nucleotides are interchangeable and which DNA modifications are desirable for a specific purpose. It is also noteworthy that the ~3.8 kb BclI spiramycin resistance gene-containing restriction fragment is not limited to a particular position on a cloning vector, as long as the critical vector-controlled functions are not disrupted. Those skilled in the art understand or can readily determine which sites on a vector are advantageous for the ligation or insertion of a particular spiramycin resistance gene-containing restriction fragment.

Although the above-described vectors comprise the Streptomyces replicon derived from plasmid pIJ702, a variety of known Streptomyces replicons can be used to construct similar vectors. Table 1 is an illustrative, but not comprehensive, listing of Streptomyces plasmids from which additional functional Streptomyces replicons can be obtained. Those skilled in the art recognize that all or part of the plasmids may be used to construct vectors exemplifying the present invention so long as the replicon function is not disrupted. The plasmid-containing host and depository accession number are also listed in Table 1.

TABLE 1

Streptomyces Plasmids

| Plasmid | Host | Accession Number |
|---------|------|------------------|
| SCP2 | *Streptomyces coelicolor* A3(2) | NRRL[1] 15042 |
| SCP2* | *Streptomyces coelicolor* M110 | NRRL 15041 |
| pEL7 | *Streptomyces ambofaciens*/pEL7 | NRRL 12523 |
| pUC6 | *Streptomyces espinosus* | NRRL 11439 |
| pUC3 | Streptomyces 3022A | NRRL 11441 |
| SLP1 | *Streptomyces lividans* | NCIB[2] 11417 |
| pNM100 | *Streptomyces virginiae* | NRRL 15156 |
| pEL103 | *Streptomyces granuloruber* A39912.13/pEL103 | NRRL 12549 |

[1]Agricultural Research Culture Collection (NRRL), 1815 North University Street, Peoria, Illinois 61604, United States of America
[2]National Collection of Industrial Bacteria (NCIB), Torry Reserch Station, Post Office Box 31, 135 Abbey Road, Aberdeen AB98DG, Scotland, United Kingdom Phage φC31 is a well-known Streptomyces phage that is an excellent source of starting material for constructing integrative spiramycin resistance-conferring vectors that further exemplify the present invention. A derivative of phage φC31, phasmid pKC331, is especially preferred for constructing such integrating vectors and can be obtained from *E. coli* K12 BE447/pKC331, a strain deposited and made part of the permanent stock culture collection of the aforementioned Northern Regional Research Laboratory under the accession number NRRL B-15828. Ligation of the ~37 kb PstI restriction fragment of phasmid pKC331 to the ~4.7 kb spiramycin resistance-conferring PstI restriction fragment of plasmid pNAS105 results in the illustrative phasmids pNAS121 and pNAS122. These phasmids are integrative vectors which confer spiramycin resistance to Streptomyces and thus further exemplify the present invention.

The vectors of the present invention comprise a Streptomyces replicon and a spiramycin resistance-conferring restriction fragment. Because amplification and manipulation of plasmids is done faster and more efficiently in *E. coli* than in Streptomyces, it is convenient to add DNA sequences that also allow for replication in *E. coli*. Thus, the additions of functional replicon-containing and antibiotic resistance-conferring restriction fragments from *E. coli* plasmids such as, for example, pBR322, pACYC184, pBR325, pBR328 and the like are highly advantageous and add to the general utility of the present illustrative vectors.

The vectors used in the present method confer spiramycin resistance to spiramycin-sensitive Streptomyces or related host cells. Although 25 μg/ml of spiramycin is generally toxic to spiramycin-sensitive Streptomyces, vectors of the present invention confer resistance to levels approaching 100 μg/ml of spiramycin. The preferred spiramycin concentration for purposes of selection for other Streptomyces species is readily determined by procedures well-known in the art. While all embodiments of the present invention are useful, some of the recombinant DNA cloning vectors and transformants are preferred. Accordingly, preferred vectors and transformants are listed in Table 2.

TABLE 2

Preferred Vectors and Transformants

| Vector | Transformant |
|--------|--------------|
| pNAS105 | *Streptomyces ambofaciens* |
| pNAS105 | *Streptomyces lividans* |
| pNAS105 | *Streptomyces griseofuscus* |
| pNAS106 | *Streptomyces griseofuscus* |
| pNAS107 | *Streptomyces griseofuscus* |

TABLE 2-continued

Preferred Vectors and Transformants

| Vector | Transformant |
|---|---|
| pNAS108 | *Streptomyces griseofuscus* |
| pNAS109 | *Streptomyces griseofuscus* |

The method and recombinant DNA cloning vectors of the present invention are not limited for use in a single species or strain of Streptomyces. To the contrary, the method and the vectors are broadly applicable and can be used with spiramycin-sensitive host cells of many Streptomyces taxa, particularly restrictionless strains of economically important taxa that produce antibiotics such as aminoglycoside, macrolide, β-lactam, polyether and glycopeptide antibiotics. Such restrictionless strains are readily selected and isolated from Streptomyces taxa by conventional procedures well-known in the art (Lomovskaya et al., 1980, Microbiological Reviews 44:206). Host cells of restrictionless strains lack restriction enzymes and, therefore, do not cut or degrade plasmid DNA upon transformation. For purposes of the present application, host cells containing restriction enzymes that do not cut any of the restriction sites of the present vectors are also considered restrictionless.

Preferred host cells of restrictionless strains of spiramycin-sensitive Streptomyces taxa that produce aminoglycoside antibiotics, and in which the present method is especially useful and the present vectors can be transformed, include restrictionless cells of, for example: *Streptomyces kanamyceticus* (kanamycins), *S. chrestomyceticus* (aminosidine), *S. griseoflavus* (antibiotic MA 1267), *S. microsporeus* (antibiotic SF-767), *S, ribosidificus* (antibiotic SF733), *S. flavopersicus* (spectinomycin), *S. spectabilis* (actinospectacin), *S. rimosus* forma *paromomycinus* (paromomycins, catenulin), *S. fradiae* var. *italicus* (aminosidine), *S. bluensis* var. *bluensis* (bluensomycin), *S. catenulae* (catenulin), *S. olivoreticuli* var. *cellulophilus* (destomycin A), *S. lavendulae* (neomycin), *S. albogriseolus* (neomycins), *S. tenebrarius* (tobramycin, apramycin), *S. albus* var. *metamycinus* (metamycin), *S. hygroscopicus* var. *sagamiensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var. *limoneus* (validamycins), *S. rimofaciens* (destomycins), *S. hygroscopicus* forma *glebosus* (glebomycins), *S. fradiae* (hybrimycins neomycins), *S. eurocidicus* (antibiotic A16316-C), *S. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins), *S. hofuensis* (seldomycin complex) and *S. canus* (ribosyl paromamine).

Preferred host cells of restrictionless strains of spiramycin-sensitive Streptomyces taxa that produce macrolide antibiotics, and in which the present method is especially useful and the present vectors can be transformed, include restrictionless cells of, for example: *Streptomyces caelestis* (antibiotic M188), *S. platensis* (platenomycin), *S. rochei* var. *volubilis* (antibiotic T2636), *S. venezuelae* (methymycins), *S. griseofuscus* (bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S. cinerochromogenes* (cineromycin B), *S. albus* (albomycetin), *S. felleus* (argomycin, picromycin), *S. rochei* (lankacidin, borrelidin), *S. violaceoniger* (lankacidin), *S. griseus* (borrelidin), *S. maizeus* (ingramycin), *S. albus* var. *coilmyceticus* (coleimycin), *S. mycarofaciens* (acetyl-leukomycin, espinomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. *suragaoensis* (kujimycins), *S. kitasatoensis* (leucomycin), *S. narbonensis* var. *josamyceticus* (leucomycin A3, josamycin), *S. albogriseolus* (mikonomycin), *S. bikiniensis* (chalcomycin), *S. cirratus* (cirramycin), *S. djakartensis* (niddamycin), *S. eurythermus* (angolamycin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin), and *S. albireticuli* (carbomycin).

Preferred host cells of restrictionless strains of spiramycin-sensitive Streptomyces taxa that produce β-lactam antibiotics, and in which the present method is especially useful and the present vectors can be transformed, include restrictionless cells of, for example: *Streptomyces lipmanii* (A16884, MM4550, MM13902), *S. clavuligerus* (A16886B, clavulanic acid), *S. lactamdurans* (cephamycin C), *S. griseus* (cephamycin A, B), *S. hygroscopicus* (deacetoxycephalosporin C), *S. wadayamensis* (WS-3442-D), *S. chartreusis* (SF 1623), *S. heteromorphus* and *S. panayensis* (C2081X); *S. cinnamonensis, S. fimbriatus, S. halstedii, S. rochei* and *S. viridochromogenes* (cephamycins A, B); *S. cattleya* (thienamycin); and *S. olivaceus, S. flavovirens, S. flavus, S. fulvoviridis, S. argenteolus* and *S. sioyaensis* (MM 4550 and MM 13902).

Preferred host cells of restrictionless strains of spiramycin-sensitive Streptomyces taxa that produce polyether antibiotics, and in which the present method is especially useful and the present vectors can be transformed, include restrictionless cells of, for example: *Streptomyces albus* (A204, A28695A and B, salinomycin), *S. hygroscopicus* (A218, emericid, DE3936), A120A, A28695A and B, etheromycin, dianemycin), *S. griseus* (grisorixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a) and *S. violaceoniger* (nigericin).

Preferred host cells of restrictionless strains of spiramycin-sensitive Streptomyces taxa or related genera such as, for example, Nocardia that produce glycopeptide antibiotics, and in which the present method is especially useful and the present vectors can be transformed, include restrictionless cells of, for example: *Nocardia orientalis* and *Streptomyces haranomachiensis* (vancomycin); *Nocardia candidus* (A-35512, avoparcin), *S. eburosporeus* (LL-AM 374), *S. virginiae* (A41030) and *S. toyocaensis* (A47934).

Preferred host cells of restrictionless strains of spiramycin-sensitive Streptomyces taxa, and in which the present method is especially useful and the present vectors can be transformed, include restrictionless cells of, for example: *Streptomyces coelicolor, S. granuloruber, S. roseosporus, S. lividans, S. tenebrarius, S. acrimycins, S. glaucescens, S. parvilin, S. pristinaespiralis, S. violaceoruber, S. vinaceus, S. espinosus, S. azureus, S. griseofuscus, S. fradiae, S. ambofaciens* and *S. toyocaensis.*

The method and recombinant DNA cloning vectors of the present invention have broad utility and help fill the need for suitable cloning vehicles for use in Streptomyces and related organisms. Moreover, the ability of the present vectors to confer spiramycin resistance provides a functional means for selecting transformants. This is important because of the practical necessity for determining and selecting the particular cells that have acquired vector DNA.

Additional DNA segments, that lack functional tests for their presence, can also be inserted onto the present vectors, and then transformants containing the non-selectable DNA can be isolated by spiramycin selection. Such non-selectable DNA segments can be inserted at any site, except within regions necessary for plasmid function and replication or within the spiramycin resistance-conferring gene, and include, but are not limited to, genes that specify antibiotic modification enzymes and regulatory genes of all types.

More particularly, a non-selectable DNA segment that comprises a gene is inserted on a plasmid such as, for example, plasmid pNAS108 at the central ClaI restriction site of the thiostrepton resistance gene. Such an insertion inactivates the thiostrepton resistance gene and thus allows for the easy identification of transformants containing the recombinant plasmid. This is done by first selecting for spiramycin resistance and, secondarily, identifying those spiramycin-resistant transformants that are not resistant to thiostrepton. Therefore, the ability to select for spiramycin resistance in Streptomyces and related cells allows for the efficient isolation of the extremely rare cells that contain the particular non-selectable DNA of interest.

The functional test for spiramycin resistance, as described herein above, is also used to locate DNA segments that act as control elements and direct expression of an individual antibiotic resistance-conferring gene. Such segments, including, but not limited to, promoters, attenuators, repressor and inducer binding-sites, ribosomal binding-sites and the like, are used to control the expression of other genes in cells of Streptomyces and related organisms.

The spiramycin resistance-conferring vectors of the present invention are also useful for ensuring that linked DNA segments are stably maintained in host cells over many generations. These genes or DNA fragments, covalently linked to the spiramycin resistance-conferring restriction fragment and propagated in Streptomyces, are maintained by exposing the transformants to levels of spiramycin that are toxic to non-transformed cells. Therefore, transformants that lose the vector, and consequently any covalently linked DNA, cannot grow and are eliminated from the culture. Thus, the vectors of the present invention can stabilize and maintain any DNA sequence of interest.

The method, cloning vectors and transformants of the present invention provide for the cloning of genes to improve yields of various products that are currently produced in Streptomyces and related cells. Examples of such products include, but are not limited to, Streptomycin, Cephalosporins, Actaplanin, Apramycin, Narasin, Monensin, Tobramycin, Erythromycin and the like. The present invention also provides selectable vectors that are useful for cloning, characterizing and reconstructing DNA sequences that code: for commercially important proteins such as, for example, human insulin, human proinsulin, glucagon, interferon and the like; for enzymatic functions in metabolic pathways leading to commercially important processes and compounds; or for control elements that improve gene expression. These desired DNA sequences also include, but are not limited to, DNA that codes for enzymes that catalyze synthesis of derivatized antibiotics such as, for example, Streptomycin, Cephalosporin, Apramycin, Actaplanin, Narasin, Tobramycin, Monensin and Erythromycin derivatives, or for enzymes that mediate and increase bioproduction of antibiotics or other products. The capability for inserting and stabilizing such DNA segments thus allows for increasing the yield and availability of antibiotics that are produced by Streptomyces and related organisms.

Streptomyces can be cultured in a number of ways using any of several different media. Carbohydrate sources which are preferred in a culture medium include, for example, molasses, glucose, dextrin and glycerol. Nitrogen sources include, for example, soy flour, amino acid mixtures and peptones. Nutrient inorganic salts are also incorporated and include the customary salts capable of yielding sodium, potassium, ammonium, calcium, phosphate, chloride, sulfate and like ions. As is necessary for the growth and development of other microorganisms, essential trace elements are also added. Such trace elements are commonly supplied as impurities incidental to the addition of other constituents of the medium.

Streptomyces is grown under aerobic culture conditions over a relatively wide pH range of about 5 to 9 at temperatures ranging from about 15° to 40° C. For plasmid stability and maintenance, it is desirable to start with a culture medium at a pH of about 7.2 and maintain a culture temperature of about 30° C.

The following examples further illustrate and detail the invention disclosed herein. Both an explanation of and the actual procedures for constructing the invention are described where appropriate.

The following solutions are referred to throughout the examples and are presented here for clarity.

| 1. P medium (~100 ml): | |
|---|---|
| Ingredient | Amount |
| Sucrose | 10.3 g |
| $K_2SO_4$ | 0.025 g |
| Trace element solution (see #3) | 0.2 ml |
| $MgCl_2.6H_2O$ | 0.203 g |
| Water to | 80 ml |
| After autoclaving add: | |
| $KH_2PO_4$ (0.5%) | 1 ml |
| $CaCl_2.2H_2O$ (3.68%) | 10 ml |
| (N—tris(hydroxymethyl)-methyl-2-amonoethane sulphonic acid) "TES" buffer, 0.25 M, pH = 7.2 | 10 ml |

| 2. L medium (~111 ml): | |
| --- | --- |
| Ingredient | Amount |
| Sucrose (10.3%) | 100 ml |
| TES buffer, pH 7.2 (0.25 M) | 10 ml |
| $K_2SO_4$ (2.5%) | 1 ml |
| Trace element solution (see #3) | 0.2 ml |
| $KH_2PO_4$ (0.5%) | 1 ml |
| $MgCl_2$ (2.5 M) | 0.1 ml |
| $CaCl_2$ (0.25 M) | 1 ml |
| Lysozyme | 1 mg/ml |

The L medium is filter sterilized after preparation.

| 3. Trace element solution (~1 liter): | |
| --- | --- |
| Ingredient | Amount |
| $ZnCl_2$ | 40 mg |
| $FeCl_3.6H_2O$ | 200 mg |
| $CuCl_2.2H_2O$ | 10 mg |
| $MnCl_2.4H_2O$ | 10 mg |
| $Na_2B_4O_7.10H_2O$ | 10 mg |
| $(NH_4)_6Mo_7O_{24}.4H_2O$ | 10 mg |
| $H_2O$ to | 1 l. |

| 4. R2 Regeneration Medium (~1 liter): | |
| --- | --- |
| Ingredient | Amount |
| Sucrose | 103 g |
| $K_2SO_4$ | 0.25 g |
| Trace element solution | 2 ml |
| $MgCl_2.6H_2O$ | 10.12 g |
| glucose | 10 g |
| L-asparagine.$1H_2O$ | 2.0 g |
| casamino acids | 0.1 g |
| Agar | 22 g |
| Water to | 700 ml |
| After autoclaving add: | |
| $KH_2PO_4$ (0.05 g/100 ml) | 100 ml |
| $CaCl_2$ (2.22 g/100 ml) | 100 ml |
| TES Buffer (5.73 g/100 ml, pH = 7.2) | 100 ml |
| NaOH (5N) | 1 ml |

| 5. T medium (~14.5 ml): | |
| --- | --- |
| Ingredient | Amount |
| Sucrose (10.3%) | 2.5 ml |
| Distilled water | 7.5 ml |
| Trace element solution | 2 μl |
| $K_2SO_4$ (2.5%) | 10 μl |
| $CaCl_2$ (5 M) | 215 μl |
| Tris-maleic acid, pH = 8 (1 M) | 538 μl |
| Polyethylene glycol 1000 (Sigma, St. Louis, Missouri) | 3.58 g |

All components were sterilized by autoclaving. The liquid components were mixed and then added to the appropriate amount of molten polyethylene glycol. The first four ingredients may be pre-mixed and stored at room temperature for at least one month.

| 6. Yeast Extract - Malt Extract (YEME, ~1 liter): | |
| --- | --- |
| Ingredient | Amount |
| Yeast extract | 3 g |
| Peptone | 5 g |
| Malt extract | 3 g |
| Glucose | 10 g |
| $H_2O$ to | 1 l |

7. YEME+34% Sucrose Liquid Complete Medium is YEME with 340 g/liter of sucrose.

| 8. YMX Media (~l): | |
| --- | --- |
| Ingredient | Amount |
| Yeast extract | 3 g |
| Malt extract | 3 g |
| Glucose | 2 g |
| Agar | 20 g |
| $H_2O$ to | 1 l |

| 9. Regeneration Medium Soft Agar Overlays (R2 soft 1 liter) | |
| --- | --- |
| Ingredient | Amount |
| Sucrose | 103 g |
| $MgCl_2.6H_2O$ | 10.12 g |
| $CaCl_2$ | 2.22 g |
| TES buffer, pH 7.2 (0.25 M) | 100 ml |
| Agar | 4.1 g |
| $H_2O$ to | 1 l |

EXAMPLE 1

Isolation of Plasmid pNAS105

A. Culture of *Streptomyces griseofuscus*/pNAS105

A vegetative inoculum was conventionally prepared by growing *Streptomyces griseofuscus*/pNAS105 (NRRL 15919) under submerged conditions for 20 hours at 30° C. in TSB* medium (Tryticase Soy Broth) supplemented with 0.4% glycine, 0.005 M $MgCl_2$ plus 25 μg/ml thiostrepton**.

*TSB is made at 30 g/l and can be obtained from: Bethesda Research Laboratories, Inc., P.O. Box 577, Gaithersburg, Md. 20760.
**Thiostrepton can be obtained from E. R. Squibb and Sons, Inc., Princeton, N.J. 08540.

B. Isolation of Plasmid DNA

The culture of Example 1A was homogenized and used to inoculate 500 ml of TSB plus 0.005 M $MgCl_2$, 0.4% glycine and 25 μg/ml thiostrepton. The culture was incubated at 30° C. for 48 hours. The cells were collected by centrifugation and washed with a 10% glycerol solution and then suspended in 50 ml TE (10 mM Tris-HCl pH 8.0, 1 mM EDTA) containing 34% sucrose. Ten ml of 0.25 M EDTA (pH 8.0) and 5 ml of a 50 mg/ml solution of lysozyme in 0.01 M Tris-HCl, pH 8.0 were added. After mixing and incubating at 30° C. for 10-30 minutes, 50 ml of ice cold TE plus 34% sucrose were added. The cells were placed in an ice bath and 30 ml ice cold 0.25 M EDTA, pH 8.0 plus 5 ml ice cold 0.01M Tris-HCl, pH 8.0 were added and mixed. Next, the solution was distributed into precooled centrifuge tubes (25 ml/tube). To each tube 3.6 ml 10% SDS and 7.2 ml ice cold 5 M NaCl were added and the tubes inverted slowly several times. The mixture was incubated at 4° C. for 2-15 hours and then centrifuged at 4° C. The supernatants were collected and cold 30% PEG (polyethylene glycol) 6000 was added to a final concentration of 10%; this mixture was incubated for 2 to 15 hours at 4° C.

The precipitate was collected by centrifugation and resuspended in 6 ml of a solution containing 0.03 M Tris-HCl pH 8.0, 0.005M EDTA pH 8.0 and 0.05 M NaCl. Cesium chloride was added to a density of 1.625 gm/ml at 20° C. and ethidium bromide was added to a concentration of 500 μg/ml. The solution was centrifuged at 40,000 rpm for 60 hours at 20° C. The plasmid band was collected and ethidium bromide removed by extraction 5-7 times with iso-amyl alcohol. The sample was dialyzed against 1 liter TE overnight at 4° C.

Following dialysis, the DNA was precipitated by the addition of 0.1 volume 3 M NaOAc and 3 volumes 95% ethanol and incubation on dry ice until the mixture was frozen. The precipitate was collected by centrifugation, resuspended in 0.3 ml of 0.3 M NaOAc and extracted with an equal volume of phenol saturated with TE. The aqueous phase was extracted with ether and the DNA precipitated by the addition of 3 volumes 95% ethanol and incubation as described above. The precipitate was collected by centrifugation, washed with 3 volumes 70% ethanol at −20° C. for 20 minutes. The precipitate was collected by centrifugation and the pellet dried and resuspended in 0.5 ml TE. A restriction site and function map of plasmid pNAS105 is presented in FIG. 1 of the accompanying drawings.

EXAMPLE 2

Construction of Plasmid pNAS106

A. BclI Digestion of Plasmid pNAS105

Approximately 0.3 μg (1 μl) of the plasmid pNAS105 was mixed with 10 μl of 10× reaction buffer (60 mM Tris-HCl, pH 7.5; 60 mM $MgCl_2$; 60 mM NaCl; and 60 mM 2-mercaptoethanol), 2 μl of 1 mg/ml gelatin, 2 μl 1 M NaCl, 0.5 μl BclI (18.2 units) restriction enzyme* and 12.5 μl $H_2O$ and incubated at 37° C. for 1 hour. Ten μg yeast soluble tRNA and 0.3 ml of 0.3 M NaOAc were added and the mixture was extracted with an equal volume of phenol saturated with TE. The aqueous phase was extracted with ether and the DNA was precipitated and washed with ethanol as described in Example 1B. The dried DNA pellet was resuspended in 8.5 μl TE.

*Restriction enzymes can be obtained from the following sources:
New England Bio Labs., Inc., 32 Tozer Rd., Beverly, Mass. 01915
Boehringer-Mannheim Biochemicals, P.O. Box 50816, Indianapolis, Ind. 46250
Bethesda Research Laboratories Inc., P.O. Box 577, Gaithersburg, Md. 20760

B. Isolation of Plasmid pIJ702

*Streptomyces lividans* TK23/pIJ702 was cultured and plasmid pIJ702 isolated in substantial accordance with the teaching of Example 1. Plasmid pIJ702 can also be isolated from *S. lividans*/pIJ702 (ATCC 39155) and used for purposes of this invention. *S. lividans* TK23/pIJ702 was used as the inoculum and the culture was grown in YEME plus 34% sucrose, 0.005 M $MgCl_2$, 0.5% glycine and 25 μg/ml thiostrepton.

C. BglII Digestion of Plasmid pIJ702

Approximately 0.275 μg (1 μl) plasmid pIJ702 DNA was mixed with 2 μl of 10× reaction buffer, 2 μl of 1 mg/ml gelatin, 1.2 μl 1 M NaCl, 1 μl BglII (8 units) restriction enzyme and 13 μl $H_2O$. The mixture was incubated at 37° C. for 1 hour. The digested plasmid DNA was treated with calf intestine alkaline phosphatase (CAP) according to the following procedure. To the digested DNA mixture, 1 μl of 10× kinase buffer (0.5 M Tris-HCl, pH 9.5; 0.1 M $MgCl_2$; and 50 mM DTT) was added. Approximately 0.17 units CAP (in 1× kinase buffer) were added and the mixture incubated at 65° C. for 30 minutes. The CAP addition and incubation step were twice repeated. The DNA was extracted as described in Example 2A and the dried DNA pellet was resuspended in 5.5 μl TE.

D. Ligation

Approximately 2 μl of the BglII-CAP-treated plasmid pIJ702 were mixed with 1 μl of the BclI-treated plasmid pNAS105, 2 μl of 10× C buffer (0.66 M Tris-HCl, pH 7.5; 0.066 M $MgCl_2$; and 0.1 M DTT), 2 μl of 1 mM ATP, 1 μl T4 DNA ligase (2 units) and 12 μl $H_2O$ and incubated overnight at 16° C.

EXAMPLE 3

Construction of *Streptomyces griseofuscus*/pNAS106

A. Growth of Cultures for Preparation of Protoplasts

A vegetative inoculum was conventionally prepared by growing *Streptomyces griseofuscus* C581 (ATCC 23916) under submerged conditions for 20 hours at 30° C. in TSB supplemented with 0.4% glycine. The procedure for protoplasting *S. griseofuscus* is generally performed as follows. A culture of *S. griseofuscus* was inoculated on YMX agar medium (0.3% yeast extract, 0.3% malt extract, 0.2% dextrose and 2% agar) and incubated at 30° C. for approximately 48 hours. A single bacterial colony from the plate was then inoculated into 10 ml TSB; the culture was homogenized and then incubated at 30° C. overnight. About 4 ml of the overnight culture were homogenized, added to 100 ml TSB supplemented with 0.4% glycine and then incubated overnight at 30° C. This procedure was repeated, using the fresh overnight culture. About 50 ml of 50% (v/v) glycerol were then added to the culture and 15 ml samples were frozen and stored for up to six months at −20° C. The frozen cells were thawed by placing the tube at room temperature in a beaker of water. The cells were then harvested in a bench top centrifuge and washed three times in 10 ml of 10.3% sucrose. The cell pellet was resuspended in 10 ml of P medium supplemented with lysozyme (1 mg/ml) and incubated at 30° C. for 2 hours. The mixture was then centrifuged to pellet the protoplasts. The pellet was washed three times, using 10 ml P medium and vortexed into solution each wash. The protoplasts were resuspended in 2 ml P medium for subsequent transformation.

B. Transformation

About 10 μl of plasmid DNA in ligation buffer and 150 μl of *S. griseofuscus* protoplasts were mixed together and 101 μl 50% PEG 1000 in P medium added. After a 1-2 minute incubation, the volume was adjusted to 1 ml with P medium. The cells were plated on R2 medium and incubated at 30° C. overnight.

C. Analysis of *Streptomyces griseofuscus* Transformants

A R2 soft agar overlay containing thiostrepton to make the final plate concentration 25 μg/ml was added. The plates were incubated at 30° C. for 7-10 days. Spiramycin resistant transformants were identified by replica plating onto TSB medium containing 25 μg/ml spiramycin. The resulting spiramycin resistant *S. griseofuscus* colonies can be isolated according to known procedures, cultured and then conventionally identified as described below. The transformant culture can then be used for subsequent production and isolation of plasmid DNA.

The resultant transformants were cultured on TSB agar supplemented with spiramycin (25 μg/ml) to obtain single colonies for plasmid isolation for analysis. These single colonies were used to inoculate 5 ml TSB containing thiostrepton (25 μg/ml). The cultures were homogenized and then grown overnight at 30° C. on a culture wheel. The cells were pelleted and resuspended in a solution of 10.3% sucrose (3 ml/gm wet weight). To 400 μl of the cells, 100 μl of a 5× lysozyme solution were added (5× lysozyme is 0.125M Tris HCl, pH 8.0; 0.125M EDTA, pH 8; 10 mg/ml lysozyme; and 10.3% sucrose.) After incubation at 37° C. for 10 minutes, 300 μl of lytic solution (lytic solution is 0.3 M NaOH, 1% SDS prewarmed to 50° C.) were added and the mixture vortexed. After incubation at 80° C. for 10 minutes, the mixture was cooled to room temperature and then extracted with phenol saturated with TE. To 700 μl of the aqueous phase, 70 μl of 3 M NaOAC and 700 μl isopropanol were added. After mixing, the sample was incubated at room temperature for 30 minutes. The DNA was collected by centrifugation and dissolved in 500 μl TE. Next, the DNA was reprecipitated by the addition of 25 μl 100 mM spermine and incubated at room temperature for 15 minutes. The precipitate was collected by centrifugation, and the pellet washed with 1 ml of a solution containing 75% ethanol, 0.3 M NaOAC, pH 8 and 10 mM MgCl₂. The sample was again pelleted by centrifugation and the pellet resuspended in 25 μl TE containing 10 μg/ml RNase. Restriction enzyme cutting and electrophoretic analysis of the reaction products were used to determine plasmid structure.

EXAMPLE 4

Construction of Plasmid pNAS107

A. PstI Digestion of Plasmid pNAS105 and Purification of the ~4.7 kb PstI Restriction Fragment Approximately 6 μg of the plasmid pNAS105 (20 μl ) were mixed with 4 μl 10× reaction buffer, 4 μl 1 mg/ml gelatin, 4 μl 1 M NaCl, 1.5 μl PstI (75 units) restriction enzyme and 6 μl H₂O and incubated at 37° C. for 3 hours. The reaction mixture was loaded into an agarose gel and the desired ~4.7 kb PstI restriction fragment purified in substantial accordance with the teaching of Patterson et al., *Proc. Natl. Acad.Sci* 76: 615 (1979). The approximately 1.5 μg of the ~4.7 kb PstI restriction fragment obtained were suspended in 15 μl TE buffer and stored at −20° C.

B. PstI Digestion of Plasmid pIJ702 and Ligation

Approximately 0.55 μg (2 μl ) plasmid pIJ702 DNA was mixed with 2 μl of 10' reaction buffer, 2 μl of 1 mg/ml gelatin, 2 μl of 1 M NaCl, 0.5 μl PstI (25 units) restriction enzyme and 12 μl H₂O. The mixture was incubated at 37° C. for 2 hours and then treated with calf intestine akaline phosphatase and purified as described in Example 2C. The PstI cleaved pIJ702 plasmid was resuspended in 10 μl TE. About 1 μl of the PstI-CAP-treated plasmid pIJ702 was mixed with 1 μl of the ~4.7 kb PstI restriction fragment in substantial accordance with the teaching of Example 2D except that the ligation volume was 10 μl.

EXAMPLE 5

Construction of Plasmids pNAS108 and pNAS109

A. BclI Partial Digestion of the ~4.7 kb PstI Restriction Fragment

About 6 μl (0.6 μg) of the ~4.7 kb PstI restriction fragment isolated above were treated with CAP as in Example 2C except 0.5 μl of 10× kinase buffer and 3 μl H₂O were added. The CAP-treated fragment was then digested with BclI restriction enzyme using conditions to generate partial digestion. Approximately 0.3 μg of the ~4.7 kb CAP-treated PstI fragment was mixed with 2 μl of 10× reaction buffer, 2 μl of 1 mg/ml gelatin, 0.5 μl BclI (18.2 units) restriction enzyme, 2 μl of 1 M NaCl and 6.2 μl H₂O and incubated at 37° C. for 3 minutes.

BglII Digestion of Plasmid pIJ702

Plasmid pIJ702 was digested with BglII, treated with CAP and purified as in Example 2C except 0.55 μg (2 μl ) plasmid pIJ702 was used. The BglII-cleaved plasmid was resuspended in 10 μl TE.

C. Ligation

These ligations were carried out in substantial accordance with the method of Example 2D with the following exceptions. One μl BglII treated plasmid pIJ702 was mixed with 2 μl of the ~4.7 kb PstI fragment partially digested with BclI, 1 μl 10× C buffer, 1 μl 1 mM ATP, 1 μl T4 DNA ligase (2 units) and 4 μl H₂O, to generate plasmid pNAS108. The aforementioned fragments re mixed with 2 μl 10× C buffer, 2 μl of 1 mM ATP, 2 μl T4 DNA ligase and 10 μl H₂O to generate plasmid pNAS109. Plasmid pNAS108 differs from plasmid pNAS109 only in respect to the orientation of the ~4.7 kb PstI fragment (see FIGS. 3 and 4). This ligated DNA was then used to transform Streptomyces to obtain the respective plasmids.

EXAMPLE 6

Construction of Transformants *Streptomyces griseofuscus*/pNAS107, *S. griseofuscus*/pPS108 and *S. griseofuscus*/pNAS109

Each of the above constructions were separately made and analyzed in accordance with the foregoing teaching of Example 3.

EXAMPLE 7

Transformation of *Streptomyces lividans* with Plasmid pNAS105

A. Preparation and Storage of Protoplasts

A culture of *Streptomyces lividans* was grown for 40–48 hours at 30° C. in YEME+34% sucrose, 5 mM MgCl₂ and 0.5% glycine. *S. lividans* TK23 is an old and MgC12 well-known strain which is available to the public under the accession number NRRL 15826 and is on deposit and made part of the Northern Regional Research Center, Agricultural Research Service, U.S. Department of Agriculture, Peoria, Ill. 61604. Although *S. lividans* CT2 was used and exemplified in the present invention, any spiramycin senstitive, restrictionless *S. lividans* strain can be substituted and is within the scope of the present invention.

The mycelia were recovered by centrifugation (800 g for 10 minutes in a bench top centrifuge) and washed twice in 10.3% sucrose. The mycelia from 25–50 ml of culture were suspended in 3–4 ml of L medium and incubated for one hour at 32° C. During this interval the suspension was pipetted up and down once or twice to disperse clumps. Five ml of P medium were added and the protoplasts recovered by centrifugation (800 g for 10 minutes) and washed twice with 5 ml of P medium. The protoplasts were then suspended in 4 ml of P medium. If the protoplasts are not to be used immediately, the suspension can be divided into aliquots (about 1 ml) containing $5 \times 10^9 - 10^{10}$ protoplasts in sterile eppendorf tubes. The suspensions were frozen slowly by placing the tubes in a container of ice, which was in turn placed at $-70°$ C. The protoplasts were stored at this temperature until needed. The frozen suspension was thawed rapidly by immersion in a 37° C. water bath prior to use.

B. Protoplast Transformation

Approximately $5 \times 10^9$ protoplasts were pelleted by centrifugation (800 g for 10 minutes). The supernatant was decanted and the protoplasts were resuspended in the small volume of liquid remaining in the tube. Plasmid DNA in a volume not greater than 20 μl in TE buffer was added, followed immediately by the addition of 0.5 ml of T medium. The mixture was pipetted up and down once or twice to mix the contents. At this point the suspension was diluted with 0.5 to 2.5 ml of P medium and then plated. In either case, about 0.1 ml was inoculated per plate of R2 medium.

Thiostrepton resistant transformants were selected by the addition of R2 soft agar overlay containing thiostrepton to make the final plate concentration 25 μg/ml. The plates were incubated at 30° C. for 7-10 days. Spiramycin resistant transformants were identified by testing individual colonies for the ability to grow on TSB medium containing 25 μg/ml spiramycin.

EXAMPLE 8

Transformation of *Streptomyces ambofaciens*

A. Preparation of protoplasts

A culture of *Streptomyces ambofaciens* (ATCC 15154) was grown for 24 hours at 30° C. in TSB. The mycelia were homogenized and disrupted by sonication. 0.5 ml of this culture was used to inoculate 9.5 ml TSB containing 0.4% glycine. The culture was incubated at 30° C. overnight. The mycelia were again homogenized, disrupted by sonication and used as an inoculum as described above. After 16 hours at 30° C. the mycelia were homogenized, disrupted by sonication, collected by centrifugation, washed with P medium and then resuspended in P medium plus 1 mg/ml lysozyme. The culture was incubated at 0° C. for 30 minutes and the protoplasts were collected by centrifugation. The protoplasts were washed three times with P medium and then resuspended in P medium at 3 times the original culture volume.

B. Protoplast transformation

To 200 μl *S. ambofaciens* protoplasts, 4 μl (1 μg) protamine sulfate treated-sonicated calf thymus DNA (in TE), and plasmid DNA in a volume not greater than 10 μl in P medium were added. 500 μl 55% PEG 1000 were added and mixed. The mixture was plated directly in a 3 ml R2 soft agar overlay onto R2 regeneration medium. After overnight incubation at 30° C. thiostrepton was added in a R2 soft agar overlay to make the final plate concentration 25 μg/ml. The plates were incubated 7-10 days at 30° C.

Transformants were analyzed for the presence of plasmid pNAS105 by small scale plasmid DNA analysis as described in 3B.

Representative transformants constructed in accordance with the foregoing teachings of Examples 7 and 8 include, but are not limited to, the following transformants listed in Table 3.

TABLE 3
Representative Transformants

1. Streptomyces R/R$^1$ wherein R is *ambofaciens* and *lividans* and wherein R$^1$ independently is a plasmid from the group consisting of plasmids pNAS106, pNAS107, pNAS108 and pNAS109.

We claim:

1. A method for selecting a recombinant DNA-containing Streptomyces host cell, said method comprising:
   (a) transforming a spiramycin-sensitive, restrictionless Streptomyces host cell with a recombinant DNA cloning vector capable of autonomous replication in said Streptomyces host cell, said vector comprising a constructed DNA sequence that encodes a polypeptide that confers resistance to spiramycin, and
   (b) culturing said transformed-cell under growth conditions that selects for spiramycin resistance, subject to the limitation that said host cell is susceptible to transformation, cell division and cultivation.

2. The method of claim 1 wherein the recombinant DNA cloning vector is a plasmid.

3. The method of claim 2 wherein the plasmid is selected from the group consisting of pNAS105, pNAS106, pNAS107, pNAS108 and pNAS109.

4. The method of claim 2 wherein the plasmid is pNAS105.

5. The method of claim 2 wherein the plasmid is pNAS106.

6. The method of claim 2 wherein the plasmid is pNAS107.

7. The method of claim 2 wherein the plasmid is pNAS108.

8. The method of claim 2 wherein the plasmid is pNAS109.

9. The method of claim 1 wherein the transformed Streptomyces host cell is selected from the group consisting of *Streptomyces ambofaciens, Streptomyces aureofaciens, Streptomyces griseofuscus, Streptomyces lividans, Streptomyces cinnamonensis* and *Streptomyces toyocaensis.*

10. The method of claim 9 wherein the transformed host cell is *Streptomyces griseofuscus*/pNAS105.

11. The method of claim 9 wherein the transformed host cell is *Streptomyces griseofuscus*/pNAS106.

12. The method of claim 9 wherein the transformed host cell is *Streptomyces griseofuscus/pNAS*107.

13. The method of claim 9 wherein the transformed host cell is *Streptomyces griseofuscus*/pNAS108.

14. The method of claim 9 wherein the transformed host cell is *Streptomyces griseofuscus*/pNAS109.

15. The method of claim 9 wherein the transformed host cell is *Streptomyces lividans*/pNAS105.

16. The method of claim 9 wherein the transformed host cell is *Streptomyces ambofaciens*/pNAS105.

17. A DNA cloning vector used in the method of claim 1.

18. A vector of claim 17 which is selected from the group consisting cf plasmids pNAS105, pNAS106, pNAS107, pNAS108 and pNAS109.

19. The vector of claim 18 that is plasmid pNAS105.

20. The vector of claim 18 that is plasmid pNAS106.

21. The vector of claim 18 that is plasmid PNAS107.

22. The vector of claim 18 that is plasmid PNAS108.

23. The vector of claim 18 that is plasmid PNAS109.

24. A constructed DNA sequence of claim 1 that encodes a polypeptide that confers resistance to spiramycin.

25. A DNA sequence of claim 24 that encodes a polypeptide that confers resistance to spiramycin and which is an ~3.8 kb BclI restriction fragment of plasmid pNAS105.

26. A spiramycin-sensitive, restrictionless Streptomyces host cell transformed by a vector of claim 17.

27. The transformed Streptomyces host cell of claim 26 that is *Streptomyces ambofaciens*.

28. The transformed Streptomyces host cell of claim 26 that is *Streptomyces lividans*.

29. The transformed Streptomyces host cell of claim 26 that is *Streptomyces griseofuscus*.

30. A method for selecting a recombinant DNA-containing Nocardia host cell, said method comprising:
    (a) transforming a spiramycin-sensitive, restrictionless Nocardia host cell with a recombinant DNA cloning vector capable of autonomous replication in said Nocardia host cell, said vector comprising a constructed DNA sequence that encodes a polypeptide that confers resistance to spiramycin, and
    (b) culturing said transformed cell under growth conditions that selects for spiramycin resistance, subject to the limitation that said host cell is susceptible to transformation, cell division and cultivation.

31. The method of claim 30 wherein the recombinant DNA cloning vector is a plasmid.

32. A spiramycin-sensitive, restrictionless Nocardia host cell transformed by a DNA cloning vector of claim 31.

* * * * *